United States Patent [19]

Sipos

[11] Patent Number: 5,352,460

[45] Date of Patent: * Oct. 4, 1994

[54] COMPOSITIONS OF GASTRIC ACID-RESISTANT MICROSPHERES CONTAINING SALTS OF BILE ACIDS

[75] Inventor: Tibor Sipos, Lebanon, N.J.

[73] Assignee: Digestive Care Inc., Lebanon, N.J.

[*] Notice: The portion of the term of this patent subsequent to Nov. 9, 2010 has been disclaimed.

[21] Appl. No.: 65,780

[22] Filed: May 24, 1993

Related U.S. Application Data

[62] Division of Ser. No. 902,578, Jun. 22, 1992, Pat. No. 5,234,697.

[51] Int. Cl.$^5$ ................................................ A61K 9/16
[52] U.S. Cl. .................................... 424/490; 424/486; 424/495
[58] Field of Search ....................... 424/490, 497, 486; 514/182, 887

[56] References Cited

U.S. PATENT DOCUMENTS 5,260,074 11/1993 Sipos ................................ 424/497

FOREIGN PATENT DOCUMENTS 0321527 6/1988 European Pat. Off. .

*Primary Examiner*—G. S. Kishore
*Assistant Examiner*—William E. Benston, Jr.

[57] ABSTRACT

Disclosed are gastric acid-resistant polymer-coated ursodeoxycholate compositions, process for their preparations and methods of treating digestive disorders, impaired liver function, autoimmune diseases of the liver and biliary tract, prevention of colon cancer following cholecystectomy, cystic fibrosis, dissolving gallstones and regulating dietary cholesterol absorption by administering said compositions to a mammal in need of such treatment.

11 Claims, No Drawings

COMPOSITIONS OF GASTRIC ACID-RESISTANT MICROSPHERES CONTAINING SALTS OF BILE ACIDS

This is a continuation of divisional application under 37 CFR 1.60 of prior application Ser. No. 07/902,578 filed Jun.22, 1992 now U.S. Pat. No.5,234,697.

BACKGROUND OF THE INVENTION

1. Field of the Invention

This invention relates to salts of ursodeoxycholic acid compositions for ingestion by a mammal, a process for preparing said compositions, and a method for treating digestive disorders, impaired liver function, autoimmune diseases of the liver and biliary tract, prevention of colon cancer following cholecystectomy, cystic fibrosis, dissolving gallstones, and regulating dietary cholesterol absorption by administering said compositions to a mammal in need of such treatment.

2. Reported Developments

It is known in the prior art that ursodeoxycholic acid (hereinafter UDCA) administered to mammals can remedy various diseased conditions of the liver, gallstones, liver toxicity due to toxic metabolites, alcohol induced hang-over, drug related toxicity, colon cancer following gallbladder surgery, and deficiency associated with poor digestion of fats and lipids in the intestine. UDCA requires the presence of certain conditions in order for it to be safe and effective as will be described hereunder.

UDCA, conjugated-UDCA and other bile salts are produced by the patient's liver, stored in the gall bladder and released into the duodenum in response to a meal, the pH of which is slightly alkaline. Under these alkaline pH conditions UDCA is soluble and biologically active, and digestion of food by UDCA proceeds normally in the upper segment of the intestine. However, when UDCA is administered exogenously to the patient, the gastric conditions in the stomach, namely the presence of acid, will render the UDCA insoluble. The insoluble UDCA is biologically inactive. Therefore, orally administered Na-UDCA must be protected against gastric inactivation so that it remains intact during its transit through the stomach into the duodenum.

Once the exogenously introduced UDCA reaches the duodenum, another requirement must be satisfied: the UDCA must be released from its protective environment and intimately mixed with the food transferred from the stomach to effect digestion.

U.S. Pat. No. 4,079,125, incorporated herein by reference, addresses these requirements in a composition containing pancreatic enzymes, which closely approximate the behavior of Na-UDCA in the acidic environment of the stomach and in the neutral-to-basic environment of the upper intestine, and provides preparative methods for making the compositions. The compositions provided by said patent comprise: an enzyme concentrate formulated with a binder/disintegrant and is coated with a non-porous, pharmaceutically acceptable enteric coating polymer which is insoluble in the pH range of from about 1.5 to about 5 normally present in gastric fluids, and soluble at a pH of from about 6 to about 9, the normal pH range for mammalian intestinal fluids. The orally administered composition passes through the stomach while being protected against the acidic environment by its acid-insoluble coating which then disintegrates in the neutral to basic environment of the upper intestine releasing the enzymes from the composition. The process of making the compositions includes the provision of using a solvent and avoiding the presence of water in the blending step of the enzyme/binder/disintegrant, since it is believed that water deactivates some of the enzymes.

It is known that ursodeoxycholic acid is capable of augmenting liver function, dissolving gallstones and improving the nutritional state of patients having cystic fibrosis caused by hepatobiliary complications. (See for example: Ursodeoxycholic acid dissolution of gallstones in cystic fibrosis. Sahl. B., Howat, J., Webb, K., Thorax, 43:490–1(1988); Effects of Ursodeoxycholic Acid Therapy for Liver Disease Associated with Cystic Fibrosis. Colombo. C., Setchell, K. D., Podda, M., Crosignani, A., Roda A., Curcio, L., Ronchi, M. and Giunta, A., The Journal of Pediatrics, 117:482–489(1990); Effects of Ursodeoxycholic Acid Treatment on Nutrition and Liver Function in Patients with Cystic Fibrosis and Longstanding Cholestasis. Cotting, J., Lentze, M. J. and Reichen, J., Gut 31:918–921(1990). Also, UDCA has recently gained acceptance as an effective therapeutic modality to dissolve small to medium size cholesterol gallstones in gallstone afflicted patients. (See for example: The Effect of High and Low Doses of Ursodeoxycholic Acid on Gallstone Dissolution in Humans, Salen, G., Colalillo, A., Verga, D., Bagan, E., Tint, G. S. and Shefer, S., *Gastro.*, 78:1412–1418(1980); Ursodeoxycholic Acid: A Clinical Trial of a Safe and Effective Agent for Dissolving Cholesterol Gallstones, Tint, G. S., Salen, G., Colalillo, A., Graber, D., Verga, D. Speck, J. and Shefer, S., *Annals of Internal Medicine*., 91:1007–1018(1986); Clinical Perspective on the Treatment of Gallstones with Ursodeoxycholic Acid, Salen, G., *J. Clin. Gastroenterology*, 10 (Suppl. 2):S12–17(1988); Nonsurgical Treatment of Gallstones, Salen, G. and Tint, G. S., *New England J. Med*., 320:665–66(1989); and Reducing Cholesterol Levels, A. H. Weigand, U.S. Pat. No. 3,859,437. The recommended dosage is 10 to 15 mg/kg of body weight. In some patients much higher dosages (for example, about 30 mg/kg of body weight) are required to achieve limited benefits. However, in some patients undesirable side effects (such as severe diarrhea) seriously limit the use of this drug. The reasons for this wide variation of dosage requirements for therapeutic effectiveness and associated side effects are not completely understood. One hypothesis is that the acidic form of UDCA is only partially neutralized in the upper intestine to its sodium salt form. Many patients, such as patients with cystic fibrosis, pancreatitis or Billroth I & II and many elderly are deficient in bicarbonate secretion and lack neutralization capacity. These patients will only partially benefit from UDCA therapy. The insoluble acidic form of UDCA is poorly absorbed from the intestine, and a good portion of the administered dosage is excreted intact with feces. When a higher dosage of the acidic form of UDCA is administered to the patient, a large portion of it is neutralized in the distal parts of the intestine which in turn induces diarrhea, a highly undesirable side effect. Also, if the acidic form of UDCA is to be converted into its salt form in the duodenum, it will temporarily exhaust the buffering capacity of the duodenum and it will render the upper intestine partially acidic. The acidic pH impedes the function of the pancreatic enzymes and UDCA cannot emulsify fats and facilitate the hydrolysis, of lipids. Furthermore, the many therapeutic benefits derived from the salts forms of UDCA cannot be realized. Accordingly, the salt forms of UDCA should be administered to patients in need of UDCA, since only the ionized, i.e. salt form of UDCA possess the desirable biological characteristics in the upper intestine, including the following: 1) is readily absorbed from the intestine; 2) inhibits cholecystokinin release by the intestinal mucosa, thus ameliorating pain and producing symptomatic relief; 3) enhances the flow of bile which cleanses the liver cells from accumulated toxic metabolites and thus reduces liver toxicity and autoimmune diseases of the liver and biliary tract; 4) prevents the binding and absorption of deoxycholic acid in the colon, thus prevents colon cancer development; 5) prevents the crystallization of cholesterol into gallstones; 6) emulsifies fats; and 7) facilitates the hydrolysis of fat globules. U.S. Pat. No. 3,859,437 recommends the administration of a "small but effective amount sufficient to effect a reduction in the cholesterol level of said human being, of the compound 3 $\alpha$, 7$\beta$-dihydroxy-5$\beta$-cholanic acid (UDCA) and the non-toxic pharmaceutically acceptable salts thereof." However, administering the salt form of UDCA to patients has no advantage over the acidic form of UDCA and does not accomplish the desired result since the salt form of UDCA is converted back to the acidic form of UDCA by gastric acidity. Furthermore, the salt forms, i.e., sodium or potassium, of UDCA are extremely bitter-tasting, and in most patients cause esophageal reflux, nausea and vomiting. Because of these highly undesirable organoleptic and gastric side effects, the salt forms of UDCA have not gained therapeutic utility in the treatment of biliary diseases.

It has now been discovered that the problems associated with tablets and capsules containing UDCA may be overcome in a composition containing a salt of UDCA instead of the acidic form of UDCA. In accordance with the discovery, UDCA is first converted to a pharmaceutically acceptable salt, such as a sodium or a potassium salt, processed into microspheres, and coated with an acid-resistant polymer coating. Such composition overcomes the hereindescribed problems: 1) the polymer coating protects the Na-UDCA from gastric acidity and from conversion back to the insoluble acidic form; and 2) once the microspheres pass through the stomach in the duodenum, the protective coating dissolves in the neutral-to-alkaline range of the upper intestine. The microspheres disintegrate and release the Na-UDCA into the intestine within ten to thirty minutes. Once the Na-UDCA is released from the microspheres, it provides extra buffering capacity to neutralize the acid chyme and is rapidly absorbed from the intestine.

It has also been discovered that the salt of UDCA composition can be prepared into microtablets and microspheres in the presence of moisture without having detrimental effects on the bile salt composition thereby resulting in products that do not crumble upon drying or disintegrate upon initiation of the polymer coating procedure. This discovery is contrary to the teaching of the aforementioned U.S. Pat. No. 4,079,125 which requires complete exclusion of water (anhydrous condition) during the process of preparing pancreatic enzyme-containing microtablets and microspheres. It was found that anhydrous conditions leads to products that are extremely friable, tend to crumble into pieces upon drying in a fluidized bed dryer or a conventional coating pan and disintegrate upon initiation of the polymer coating step. This results in large amounts of dust and agglomeration of the beads into multiplets during the process as well as improper doses of Na-UDCA upon administration to the patient when quality control fails adequately to sort-out and discard said rejects. The bitter taste and associated gastric disadvantages of UDCA are also eliminated by the polymer coating which prevents solubilization of the product in the mouth and stomach of the patient.

Still further, it has been discovered that microspheres in the range of 10 to 40 mesh size can be prepared utilizing bile salts as seeds to build up the microspheres. Such small particle size microspheres are especially beneficial for treating bile salt deficiencies in cystic fibrosis children.

SUMMARY OF THE INVENTION

This invention will be described with particular reference to salts of ursodeoxycholic acid, however, it is to be understood that other bile salts may be used as well.

In accordance with one aspect of the invention, there is provided a microencapsulated, polymer-coated composition comprising a salt of UDCA in a novel pharmaceutical dosage form. In another aspect, the invention provides a process for preparing salts of UDCA for use in said composition. In still another aspect, the invention provides a process for the preparation of gastric acid-resistant polymer-coated bile salt-containing microspheres and microtablets. In its final aspect, the invention provides a method for treating bile salt deficiencies associated with biliary diseases in mammals, such as gallstones, liver toxicity due to toxic metabolites and autoimmune diseases of the liver and biliary tract, alcohol induced hang-over, drug related toxicity, prevention of colon cancer following cholecystectomy, deficiency associated with poor digestion of fats and lipids in the intestines, and regulating dietary cholesterol absorption.

Salts of UDCA and Preparation Thereof

The pharmaceutically acceptable, water soluble salts of UDCA and conjugated derivatives of UDCA (for example, glycyl and taurine ursodeoxycholate, N-methylglycyl and N-methyltaurine ursodeoxycholate) include the sodium, potassium and ammonium salts of UDCA and conjugated-UDCA of which the sodium salt is preferred. Suitable salt complexes of UDCA and conjugated-UDCA with organic bases may also be used including tromethamine, ethanolamine, diethanolamine and triethanolamine salts.

In preparing salts of UDCA and conjugated-UDCA, the acidic form of UDCA is dissolved in a suitable solvent followed by titration of solvated acid with a water-soluble alkaline hydroxide, carbonate, bicarbonate or buffer solution, such as sodium hydroxide, sodium carbonate, sodium bicarbonate, potassium hydroxide, potassium carbonate, potassium bicarbonate, tromethamine, and the like, until the pH of the solution reaches about 8.6. Most of the solvents are then removed form the titrated solution by evaporation or distillation and the salt of UDCA is recovered by spray drying or by lyophilizing the remaining solution.

For one modification of preparing salts of UDCA, an alcoholic solution of UDCA is percolated through a cation-exchange resin (Dowex) in its sodium form, followed by washing the column with two resin-bed volume of methanol, concentrating the methanol wash and recovering the Na-UDCA crystals from the methanolic mother liquor.

In accordance with the present invention, salts of UDCA compositions are provided which possess desirable characteristics heretobefore absent in proposed or existing prior art products.

The salts of UDCA are instantly soluble in water, while UDCA alone is essentially insoluble.

Only the salts and conjugated derivatives of UDCA are absorbed from the intestine, while the acidic form of UDCA is passed through the intestine intact, unless it is converted to the sodium salt by intestinal buffers. However, many patients, such as patients with cystic fibrosis, pancreatitis, Billroth I & II diseases and some elderly people, are deficient in bicarbonate secretion and lack neutralization capacity to convert the acidic form of UDCA to the sodium salt of UDCA. These patients will only partially benefit from the insoluble acidic form of UDCA therapy. The salt of UDCA-containing composition of the present invention overcomes this problem by being instantly soluble in the intestinal juices and is readily absorbable from the intestine. Additionally, the composition also provides extra buffering capacity to neutralize the acid chyme that is present in the intestine and re-establish the normal digestive conditions in patients deficient of intestinal buffers.

The salts of UDCA composition is microencapsulated and coated with an acid-resistant polymer-coating, which protects the composition from gastric acid and from conversion of the salts of UDCA to the insoluble acidic form of UDCA. The polymer-coated microcapsules are tasteless and the problem associated with the offensive bitter taste of the uncoated acidic form of UDCA or the uncoated salts of UDCA is thereby alleviated.

The microcapsules uniformly disperse with the food in the stomach and deliver high levels of biologically active salts of UDCA into the duodenum. Once in the duodenum, the polymer coating dissolves within about 10 to 30 minutes and the salts of UDCA are released to enhance digestion of fats and lipids. As a result, the natural digestive conditions in the intestine are reestablished. Epigastric pain, cramps, bloating, flatulence and stool frequency associated with maldigestion of fatty foods are reduced.

Soluble salts of UDCA and conjugated derivatives of UDCA are absorbed more efficiently and in a greater quantity from the intestine than the insoluble acidic form of UDCA, resulting in a more efficient stimulation of the liver enzymes to conjugate ursodiol (UDCA). The increased concentration of the conjugated ursodiol stimulates bile flow, enhances the displacement of toxic bile acid metabolites from the hepatocytes, decreases cholesterol secretion into bile, alters the cholesterol/phospholipid ratio of secreted bile and decreases the absorption of dietary cholesterol from the intestine. The overall result is decreased biliary cholesterol saturation, increased bile flow, dissolution of already formed cholesterol gallstones and protection of the liver from accumulated toxic metabolites.

Compositions of Salts of UDCA

The composition containing a salt of UDCA comprises a blend of ingredients and a coating therefor expressed in weight per weight percentages based on the total weight of the composition:

a) from about 60 to about 89% of a salt of UDCA in powder or microsphere form;
b) up to 5% of a buffering agent selected from the group consisting of about 0.25 to about 5.0% sodium carbonate (anhydrous powder), sodium bicarbonate, potassium carbonate and potassium bicarbonate and from about 0.25 to about 1.5% tromethamine, diethanolamine and triethanolamine;
c) from about 1.0 to about 16% of a disintegrant selected from the group consisting of starch and modified starches, microcrystalline cellulose and propylene glycol alginate;
d) from about 2.0 to about 19% of an adhesive polymer selected from the group consisting of polyvinylpyrrolidone, hydroxypropyl cellulose, cellulose acetate phthalate, and methyl cellulose; and
e) from about 8.0 to about 16% of a non-porous, pharmaceutically acceptable gastric acid-resistant polymer-coating which contains less than 2% talc and which is insoluble in the pH range of from about 1.5 to about 5 but is soluble in the pH range of from about 5.5 to about 9.

The Process of Making the Microsphere

In accordance with the present invention, the bile salt composition is prepared by a process comprising the steps of:

a) blending dry, powdery ingredients selected from the group consisting of (i) from about 60 to about 92% w/w of a salt or conjugated derivative of UDCA from the group consisting of sodium, potassium, ammonium, tromethamine, ethanolamine, diethanolamine and triethanolamine; (ii) up to 5% of a buffering agent selected from the group consisting of from about 0.25 to about 5.0% w/w sodium carbonate (anhydrous), sodium bicarbonate, potassium carbonate and potassium bicarbonate and from about 0.25 to about 1.5% w/w, tromethamine, diethanolamine and triethanolamine; (iii) of from about 1.0 to about 16% w/w of a disintegrant selected from the group consisting of starch and modified starches,
microcrystalline cellulose and propylene glycol alginate; and (iv) from about 2.0% to about 19% w/w of an adhesive polymer selected from the group consisting of polyvinylpyrrolidone, cellulose acetate phthalate, hydroxypropyl cellulose and methylcellulose;
b) wetting said blended ingredients with a liquid to cause the blend to stick together, wherein said liquid is selected from the group consisting of: 1%–25% w/w ethanol/75%–99% w/w 2- propanol/0.2%14 2% w/w water; 98% –99% w/w 2- propanol/0.2%–2% w/w water; 1%–25% w/w methanol/0.2% –2% w/w water/75%–98% w/w 2 propanol/1%–5% w/w ethylacetate;
c) granulating or extruding the liquid-wetted blend through a 10 to 18 mesh S/S screen;
d) converting the granules to a uniform diameter particle size;
e) compacting the uniform particles to spherical particles;
f) drying the spherical particles;
g) separating the spherical particles if not of uniform size according to desired sizes using U.S. Standard sieve screens;
h) coating the particles with a gastric acid-resistant polymer that dissolves under neutral or slightly basic conditions; and
i) drying the polymer-coated spherical particles.

DETAILED DESCRIPTION OF THE INVENTION

In preparing the bile salt containing microspheres of the present invention utilizing the extrusion, uni-sizer and marumerization process (later described) moisture must be included in the liquid or solvent-adhesive composition to render the adhesive polymer sticky enough to bind the bile salt-containing fluffy powder into a pliable, solid mass. This prevents the crumbling of the microspheres during the drying and coating process as well as allows the preparation of much smaller particle size microspheres, i.e. in the range of 10 to 80 mesh. Accordingly, it was found that the moisture level during the preparation of the composition should be in the range of from about 0.2% w/w to about 2.5% w/w, preferably, in the range of 0.2% w/w to 1.5% w/w, and most preferably in the range of 0.2% w/w to 1.0% w/w. When the compositions contained such amounts of moisture, the microspheres were found to be stable on aging and the integrity of the microspheres was preserved.

Further reference is now made to the process of preparing compositions of the present invention.

The process of manufacturing the microspheres comprises the following steps:

a) The dry, powdery ingredients are blended together in a conventional blender.

b) The blend is then wetted with a suitable liquid, hereinbefore described, that causes the dry blend to stick together. The stickiness of the blend can be tested by compressing a handful of the blend in the palm of the hand. If the composition is compressible and sticks together but readily crumbles when squeezed between the fingers, sufficient liquid has been added to the composition for processing in the subsequent granulation step.

c) The blend is granulated or extruded though a 10 to 18 mesh S/S screen using an oscillating/reciprocating granulator or a twin-screw extruder at a medium-to-high speed.

d) The granulated particles are classified in a so-called uni-sizer vessel that rotates at 15 to 45 rpm for about 5 to 10 minutes. The particles in this vessel are converted to a uniform diameter particle size.

e) The uniform particles are then compacted in a marumerizer, which is essentially a cylindrical vessel with a rotating disk at the bottom thereof, for about 15 to 90 seconds. An alternative method of compacting the microspheres can also be accomplished in a rotating conventional coating pan. In this case, the particles are tumbled in the pan for about 15 to 30 minutes, occasionally wetting the particles with a fine mist of the liquid composition (described in (b) under the Summary of the Invention).

f) The spherical particles are dried in an oven under a stream of dry air not exceeding 35° C. and 40% relative humidity.

g) The microspheres are separated according to the desired sizes using U S. Standard sieve screens.

h) The microspheres having 10 to 20 and 30 to 40 mesh size are separately coated with an acid-resistant polymer in a fluidized bed coating equipment, or in a conventional coating pan according to standard operating procedures as described in the manufacturer's instruction manual.

i) The polymer-coated microspheres are then dried in an oven under a stream of warm and dry air, not exceeding 35° C. and 40% relative humidity until all the volatile substances (moisture and solvents) are removed.

The following examples will further serve to illustrate the compositions of the present invention wherein the compositions and the process of preparing them will be described with reference to microsphere forms; however, it is to be noted that the microtablet form of the composition and the process of making it is also intended to be covered by the present invention. The process of making the microtablet form of the composition is analogous to that of making the microspheres with the exception that the 20 to 80 mesh particles are compressed together into microtablets of 0.5 mm to 2.5 mm with a suitable tablet press and polymer-coated, and should be understood by those skilled in the art.

Example I

Formula Composition (microspheres)

| Ingredients | A (uncoated) % w/w | B (coated) % w/w |
|---|---|---|
| Disintegrant | 5.0 | 4.3 |
| Sodium-Ursodeoxycholate | 89.0 | 76.7 |
| Buffering agent (anhydrous) | 3.0 | 2.6 |
| Adhesive Polymer | 3.0 | 2.6 |
| Polymer coat/talc mixture | | 13.8 |

Example II

Formula Composition (microspheres)

| Ingredients | A (uncoated) % w/w | B (coated) % w/w |
|---|---|---|
| Disintegrant | 9.0 | 7.6 |
| Sodium-Ursodeoxycholate | 82.0 | 69.5 |
| Buffering agent (anhydrous) | 1.0 | 0.8 |
| Adhesive Polymer | 8.0 | 6.8 |
| Polymer coat/talc mixture | | 15.3 |

Example III

Formula Composition (microtablets)

| Ingredients | A (uncoated) % w/w | B (coated) % w/w |
|---|---|---|
| Disintegrant | 3.0 | 2.7 |
| Sodium-Ursodeoxycholate | 92.0 | 82.1 |
| Buffering agent (anhydrous) | 1.0 | 0.9 |
| Adhesive Polymer | 3.0 | 2.7 |
| Lubricant (stearic acid) | 1.0 | 0.9 |
| Polymer coat/talc mixture | | 10.7 |

The microtablets are prepared by the following procedure: 1) grinding the dry blend of Na-UDCA/buffer/disintegrant in a centrifugal mill or impact pulverizer to a uniform particle size; 2) spraying the powdery mix with a fine mist of the adhesive polymer/liquid mixture; 3) and drying the composition, followed by blending the dried composition with a lubricant and compressing the free flowing powder into microtablets of 1.5 mm×2.0 mm with appropriate punches and dies and using a tableting press as described in U.S. Pat. No. 4,828,843 (Pich et al.) which is hereby incorporated by reference. The microtablets are polymer coated with a gastric acid-resistant polymer as described above in The Process of Making the Microspheres.

Example IV

Formula Composition (polymer coated microspheres)

| Ingredients | % w/w |
|---|---|
| Bile salt starting seed (20–40 mesh) | 12.8 |
| Disintegrant | 2.3 |
| Buffering agent (anhydrous) | 1.1 |
| Sodium-Ursodeoxycholate | 61.7 |
| Adhesive polymer mixture | 12.1 |
| Polymer coat/talc mixture | 10.7 |

The microspheres were prepared by employing a conventional coating pan. The microspheres were built up to larger particle sizes by placing the bile salt-containing 30 to 40 mesh starting seeds in the rotating coating pan, wetting the microspheres with the liquid/adhesive polymer-containing mixture, followed by slowly dusting the Na-UDCA/buffer/disintegrant composition over the tumbling and flowing bile salt seeds. The sequence of these steps is repeated until the seeds are built up into microspheres having diameters in the range of 10 to 20 mesh, preferably 14 to 16 mesh.

An alternate procedure for the preparation of the microspheres was carried out in fluidized bed coating equipment (Glatt Mfg. Co.) using a Wurster column. The starting seeds were placed in the equipment and fluidization was started. The Na-UDCA/disintegrant-/buffer/adhesive polymer mixture was sprayed on the fluidized microspheres as a homogenous mixture at a rate that allowed the growth of the starting seeds to larger microspheres.

Example V

Preparation of Bile Salt Containing Starting Seeds

| Ingredients | % w/w |
|---|---|
| Bile Salt | 60.7 |
| Disintegrant | 16.0 |
| Buffering agent (anhydrous) | 4.6 |
| Adhesive polymer mixture | 18.7 |

The process of making the bile salt-containing starting seeds consisted of: 1) blending the bile salt, disintegrant and the buffering agent together for 10 minutes; 2) spraying the composition with the adhesive polymer mixture until the powdery blend agglomerated; and 3) granulating or extruding the liquid moistened composition through a 10 or 18 mesh S/S screen using an oscillating/reciprocating granulator or a twin-screw extruder. The subsequent processing steps were the same as outlined in Steps a through g in "The Process of Making the Microspheres" under Summary of the Invention.

Example VI

Preparation of Salts of Ursodeoxycholic Acid 20g of UDCA is dissolved in 100 ml of alcohol (methanol, ethanol, isopropanol or any other suitable alcohol that is easily removed after UDCA has been neutralized) and a 10%–30% solution of hydroxide, bicarbonate or carbonate solution of Na, K, etc. is added to the reaction mixture with vigorous mixing. The UDCA solution is titrated until the pH reaches 8.6. The alcohol is removed from the reaction mixture on a rotary evaporator, and the aqueous solution is lyophilized or spray-dried to recover the Na-UDCA.

Reference is now made to the ingredients used in the above examples:

Bile Salts: Water soluble salts of UDCA and conjugated derivatives of UDCA (for example, glycyl and taurine ursodeoxycholate, N-methylglycyl and N-methyltauroursodeoxycholate) include the sodium, potassium and ammonium salts of UDCA and UDCA-conjugates of which the sodium salt is preferred. Suitable salt complexes of UDCA and UDCA-conjugates with organic bases may also be used including tromethamine, ethanolamine, diethanolamine and triethanolamine salts.

Disintegrant: Explotab (Mendell, Inc.) and microcrystalline cellulose.

Buffering agents: from about 0.25% to about 5.0% w/w %, sodium carbonate (anhydrous), sodium bicarbonate, potassium carbonate, potassium bicarbonate and based on the total weight of the composition; from about 0.25% to about 1.5% w/w % tromethamine, diethanolamine and triethanolamine based on the total weight of the composition.

Adhesive Polymeric Agents: Hydroxypropyl cellulose (Klucel HF, Hercules Co.), polyvinylpyrrolidone (Plasdone, GAF Co.), a 60:40 blend of methyl cellulose and ethyl cellulose (Dow Chem. Co.), hydroxypropyl methyl cellulose (Grades 50 and 55, Eastman Kodak Co.), cellulose acetate phthalate (Eastman Kodak Co.) and propylene glycol alginate (Kelco Co.).

Acid-resistant polymers to coat the microspheres and microtablets: hydroxypropyl methyl cellulose phthalate, Grades 50 and 55 (Eastman Kodak Co., or Shin-Etsu Chemical Co., Ltd.), Aquateric ® aqueous enteric coating polymer dispersion (FMC Corp.), Eudragit ® acrylic based polymeric dispersion (Rohm Pharma GMBH, Germany), and cellulose acetate phthalate (Eastman Kodak Co.). The following example will further illustrate the composition of the acid-resistant polymer-coatings:

Example VII

| | % w/w |
|---|---|
| Hydroxypropyl methyl cellulose phthalate (HPMCP)* | 7.5 |
| Diethyl phthalate (DEP) | 2.0 |
| Isopropyl alcohol (IPA) | 45.0 |
| Ethylacetate (EtoAc) | 45.0 |
| Talc, USP | 0.5 |

*When the hydroxypropyl methyl cellulose phthalate was replaced with cellulose acetate phthalate, an equally suitable acid-resistant polymer-coating was obtained, as long as talc was also included in the composition. The presence of talc with the film-forming polymer caused the deposition of an acid-impermeable polymer coat. When Aquateric ® or Eudragit ® aqueous enteric coating polymer dispersion was employed in place of hydroxypropyl methyl cellulose phthalate (HPMCP ), the microspheres were first sealed with a thin layer coat of the HPMCP (2–4% w/w of the microspheres) followed by coating with the Aquateric ® or Eudragit ®. The advantage of using an aqueous based polymeric dispersion is to save on solvents that are evaporated during the solvent based coating step and cut down on air pollution.

Distribution of microspheres according to sizes is shown in Table I

TABLE I

Distribution of the Microspheres According to Sizes

| Mesh Size | (mm) | Example IIB Microspheres (%) | Example IIIB Microspheres (%) |
|---|---|---|---|
| 10 | 2.00 | 6.2 | 3.3% |
| 14 | | 30.0 | 57.0% |
| 20 | 0.84 | 53.8 | 32.7% |

TABLE I-continued

Distribution of the Microspheres According to Sizes

| Mesh Size | (mm) | Example IIB Microspheres (%) | Example IIIB Microspheres (%) |
|---|---|---|---|
| 40 | 0.42 | 10.0 | 7.0% |

Method of Treating UDCA Deficiency

The composition of the present invention are orally administerable to patients having UDCA deficiency in an effective amount to treat such deficiency. The compositions are tasteless unlike the insoluble acidic form of UDCA which is associated with an offensive bitter taste. This advantage increases patient compliance in taking the medication. The microspheres are administerable admixed with food or they may be filled into gelatin capsules for administration in a conventional manner. In both methods of administration the microcapsules pass through the stomach intact, being protected by their acid-resistant coating. While in the stomach, the microcapsules uniformly disperse with the food therein and pass into the duodenum to deliver high levels of biologically active salts of UDCA. In the duodenum the polymer coating dissolves within ten to thirty minutes and the salt of UDCA is released.

The total amount of the composition required to be administered to a bile acid deficient patient will vary with the severity of the conditions, age and other physical characteristics of the patent. The physicians will prescribe the total amount, the dosage, and the frequency of administration on a patient by patient basis. Generally, for bile acid deficient patients, from about 0.15 to about 0.75 grams of the composition are administered once or twice a day. Larger amount may, however, be required for certain conditions, such as for dissolving gallstones.

For ease of administration of the compositions it is preferred to use gelatin capsules containing about 0.25 to 0.4 grams microspheres or microtablets. Gelatin capsules which disintegrate in the acidic environment of the stomach are well-known and utilized in the prior art. Microtablets are of small size, having a diameter between about 1 to 5 mm and a thickness between 0.5 to 4 mm. The tablet is prepared by conventional tableting procedure. However, the compositions of the present invention in the form of very small particle sizes may be used per se. For example, young children, handicapped individuals with certain diseases, and elderly patients are unable to swallow big gelatin capsules. Microspheres of very small sizes of the present invention could then be administered to these patients with liquid food, such as milk, apple sauce and semi-solid foods.

The advantages of the polymer-coated microspheres and microtablets over capsules and large tablets are well recognized in the administration of therapeutic medications. The microspheres and mini tablets disperse uniformly with the food in the stomach due to the smaller particle size of these particles and are more uniformly coated with the polymer coating because of their spherical shape. They also release their Na-UDCA content more readily than compressed large tablets or capsules. The microspheres are protected from gastric acidity by the acid-resistant polymer-coating during gastric transit. Once the microspheres reach the duodenum, the polymer coating dissolves under neutral-to-slightly-alkaline conditions and the microspheres discharge their bile salt content in the upper intestine within minutes. This release results in an efficient emulsification of fats and lipids, digestion of the emulsified lipids by pancreatic lipase, liquefaction of mucus that abstracts the intestinal mucosa and acceleration of the enzymatic digestion of mucopolysaccharides. As a result of this synergetic interaction between bile salts and pancreatic enzymes, mucus is lysed, and the receptor sites on the intestinal villi are exposed to the outer environment. The unblocked receptors can bind essential metabolites and transport them through the intestinal membrane into portal circulation. The net result is the normalization of the intestinal digestive functions, enhanced absorption of the liberated metabolites and the amelioration of the dyspeptic symptoms associated with the upper gastrointestinal tract.

What is claimed is:

1. A process for preparing a ursodeoxycholate composition for the treatment of ursodeoxycholic acid deficient mammals comprising the steps of:
    a) blending dry, powdery ingredients selected from the group consisting of (i) from about 60 to about 89% w/w of a salt of UDCA selected from the group consisting of sodium, potassium, ammonium, tromethamine, ethanolamine, diethanolamine and triethanolamine; (ii) up to about 5% of a buffering agent selected from the group consisting of from about 0.25 to about 5.0% w/w sodium carbonate (anhydrous), sodium bicarbonate, potassium carbonate and potassium bicarbonate and from about 0.25 to about 1.5% w/w, tromethamine, diethanolamine and triethanolamine; (iii) of from about 2 to about 19% w/w of an adhesive polymer selected from the group consisting of polyvinylpyrrolidone, cellulose acetate phthalate, hydroxypropylcellulose and methylcellulose; (iv) of from about 1 to about 16% w/w of a disintegrant selected from the group consisting of starch and modified starches, microcrystalline cellulose and propylene glycol alginate;
    b) wetting said blended ingredients with a liquid to cause the blend to stick together, wherein said liquid is selected from the group consisting of: 1%–25% w/w ethanol/75%–99% w/w 2- propanol/0.2%–2% w/w water; 98%–99% w/w 2-propanol/0.2%–2% w/w water; 1% –25% w/w methanol/0.2%–2% w/w water/75%–98% w/w 2 propanol/1%–5% w/w ethylacetate;
    c) granulating or extruding the liquid-wetted blend through a 10 or 18 mesh S/S screen;
    d) converting the granules to a uniform diameter particle size;
    e) compacting the uniform particles to spherical particles;
    f) drying the spherical particles;
    g) separating the spherical particles if not of uniform size according to desired sizes using U.S. Standard sieve screens;
    h) coating the particles with a gastric acid-resistant polymer that disintegrates under neutral or slightly basic conditions; and
    i) drying the polymer-coated spherical particles.

2. The process of claim 1 wherein said composition is in the form of microspheres having a mesh size of about 10 to 40.

3. The process of claim 1 wherein said liquid for wetting the blended ingredient comprises from about 0.2% to about 2.5% moisture.

4. The process of claim 3 wherein said moisture content is from 0.2 to 1.5%.

5. The process of claim 4 wherein said moisture content is from 0.2 to 1.0%.

6. A process for preparing a ursodeoxycholate composition for the treatment of ursodeoxycholic acid deficient mammals comprising the steps of:
   a) preparing a starting seed of the ursodeoxycholate comprising: blending the powdery salt of ursodeoxycholic acid with a disintegrant and a buffering agent;
   b) spraying said blend with a solution of an adhesive polymer until the blend agglomerates;
   c) granulating or extruding the moistened blend through a 10 or 18 mesh S/S screen;
   d) converting the granules to a uniform diameter particle size of 40 to 60 mesh;
   e) compacting the uniform particles to spherical particles;
   f) drying the spherical particles;
   g) separating the spherical particles if not of uniform size according to desired sizes using U.S. Standard sieve screens;
   h) employing said 40 to 60 mesh particles as starting seeds for the preparation of larger microspheres in the 10 to 20 mesh size range by placing the 40 to 60 mesh starting seeds in a rotating coating pan, spraying the microspheres with a liquid/adhesive polymer-containing mixture, followed by slowly dusting the buffered Na-ursodeoxycholic acid/disintegrant composition over the tumbling and flowing starting seeds until the desired particle sizes are obtained;
   i) coating the particles with a gastric acid-resistant polymer that dissolves under neutral or slightly basic conditions; and
   j) drying the polymer-coated spherical particles.

7. The process of claim 6 wherein the particle size range of said seed is from about 20 to about 40 mesh.

8. The process of claim 6 wherein said starting seed is selected from the group consisting of: sodium, potassium and ammonium salts of ursodeoxycholic acid; sodium, potassium and ammonium salts of glycyl and tauroursodeoxycholate; sodium and potassium salts of N-methylglycyl and N-methyl tauroursodeoxycholate.

9. The process of claim 6 wherein the polymer-coated spherical particles are of 10 to 20 mesh.

10. A method for treating ursodeoxycholic acid deficiency in mammals comprising: orally administering an effective amount of the composition prepared by the process of claim 1.

11. A method for treating ursodeoxycholic acid deficiency in mammals comprising: orally administering an effective amount of the composition prepared by the process of claim 6.

* * * * *